United States Patent [19]

Basso

[11] Patent Number: 4,674,507
[45] Date of Patent: Jun. 23, 1987

[54] TANNING BOOTH

[76] Inventor: Marlene Basso, 605 Grove St., Clifton, N.J. 07013

[21] Appl. No.: 263,751

[22] Filed: May 14, 1981

[51] Int. Cl.⁴ .................................... A61N 00/00
[52] U.S. Cl. .................................. 128/396; 128/395
[58] Field of Search ............ 128/395, 396, 371, 372, 128/362

[56] References Cited

U.S. PATENT DOCUMENTS

| | | | |
|---|---|---|---|
| 1,583,420 | 5/1926 | Picard | 128/396 |
| 1,669,468 | 5/1928 | Heintze | 128/396 |
| 1,755,418 | 4/1930 | Anderson | 128/395 |
| 1,772,219 | 8/1930 | Kempton | 128/372 |
| 2,611,367 | 9/1952 | Harkenrider | 128/396 |
| 2,667,169 | 1/1954 | Kambourakis | 128/372 |
| 2,954,771 | 10/1960 | Boyan | 128/396 |
| 3,648,706 | 3/1972 | Holzer | 128/395 |
| 4,100,415 | 7/1978 | Blaisdell et al. | 128/371 |
| 4,103,175 | 7/1978 | Levin | 128/371 |
| 4,246,905 | 1/1981 | Corth | 128/395 |

OTHER PUBLICATIONS

Rotheudt Enterprises Corp., Euro Tan International brochure, 1980.

Primary Examiner—Gene Mancene
Assistant Examiner—C. W. Shedd
Attorney, Agent, or Firm—Eliot S. Gerber

[57] ABSTRACT

A tanning booth is provided which creates an even tanning effect and includes either a combination of UVB and UVA lamp or a novel ultraviolet lamp emitting radiation in the specific 300–340 nm range. The booth is formed as a cylinder which is rotated at a constant speed so as to provide an even tan to a user who is stationary at the axis of the cylinder.

10 Claims, 3 Drawing Figures

TANNING BOOTH

FIELD OF THE INVENTION

This invention relates to a booth for providing a tan to the user.

BACKGROUND AND DISCUSSION OF PRIOR ART

Heretofore it was known in the art to provide fixed booths containing irradiating lamps for providing tanning rays to the user. Typical of such booths are U.S. Pat. No. 4,100,415, granted July 11, 1978, to Blaisdell, et al, U.S. Pat. No. 2,631,588, dated Mar. 17, 1953, granted to A. H. Paschell, and U.S. Pat. No. 1,583,420, dated May 4, 1926, granted to H. Picard.

In order to receive a somewhat even tan, it was necessary for the users of such prior art booths to periodically move or turn to different parts of the booth.

It was also recognized in certain prior art devices to use high intensity UVA lamps in the 320 to 400 nm range, so as to quickly energize the tanning effect. U.S. Pat. No. 4,100,415 typically discloses the use of such UVA lamps.

The use of large numbers of UVA lamps also required a closely controlled operation to prevent the overexposure to high intensity UVA range.

Certain other prior art devices, such as the tanning table, used a high plurality of UVB lamps in the relatively low, long wavelength ultraviolet range.

While such tanning tables would not subject the user to the higher intensity UVA rays, the long continuous exposure often provided an undesirable yellowing of the skin.

Now there is provided by the present invention a tanning booth which permits rapid even tanning while eliminating the undesirable effects by the prior art apparatuses.

It is therefore a principal object of the present invention to provide a tanning booth which provides an even and safer tanning effect.

It is another object of the present invention to provide a tanning booth as aforesaid which is readily constructed of readily available materials, is practical in design, and yet safe and practical in use.

SUMMARY OF THE INVENTION

Figure 1:
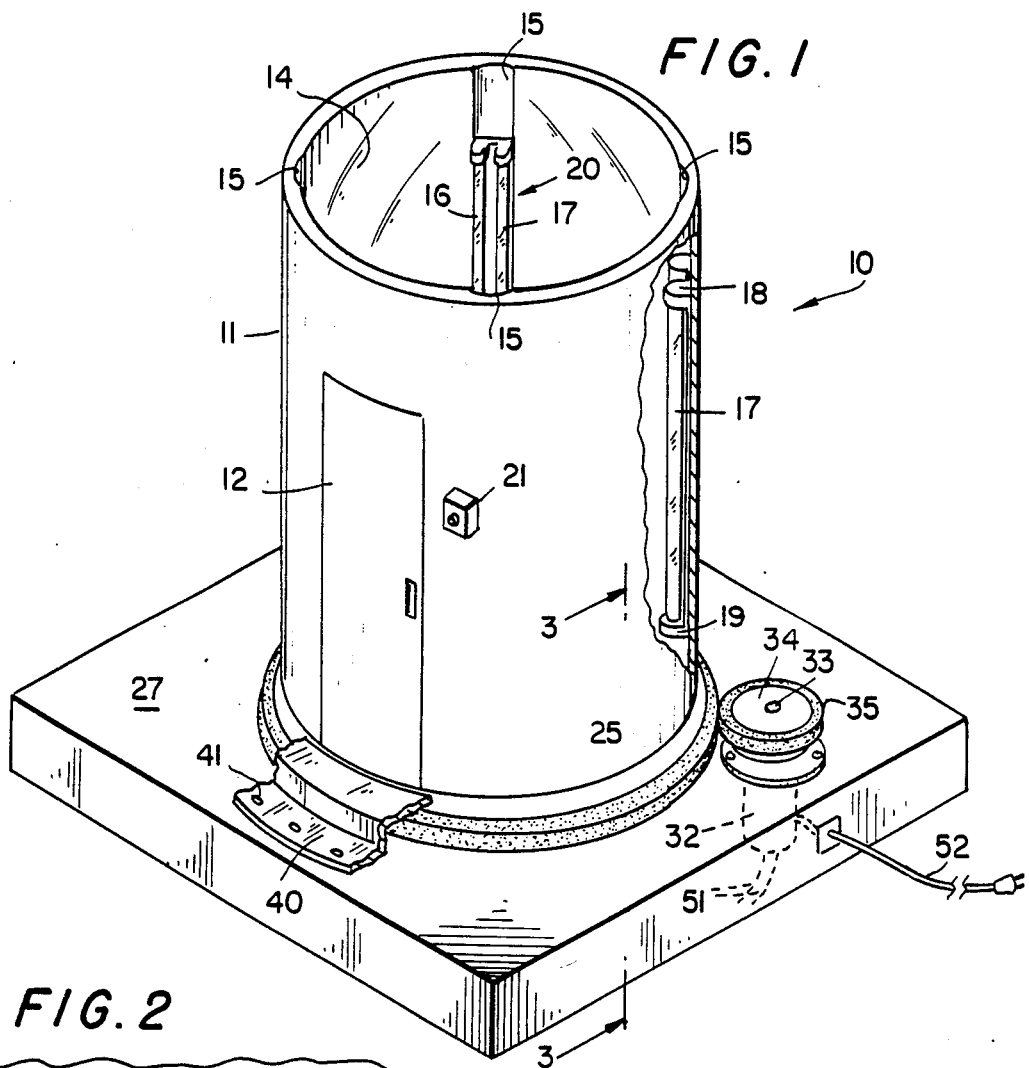
FIG. 1 is a perspective partial fragmentary view of the tanning booth of the present invention.
Figure 2:
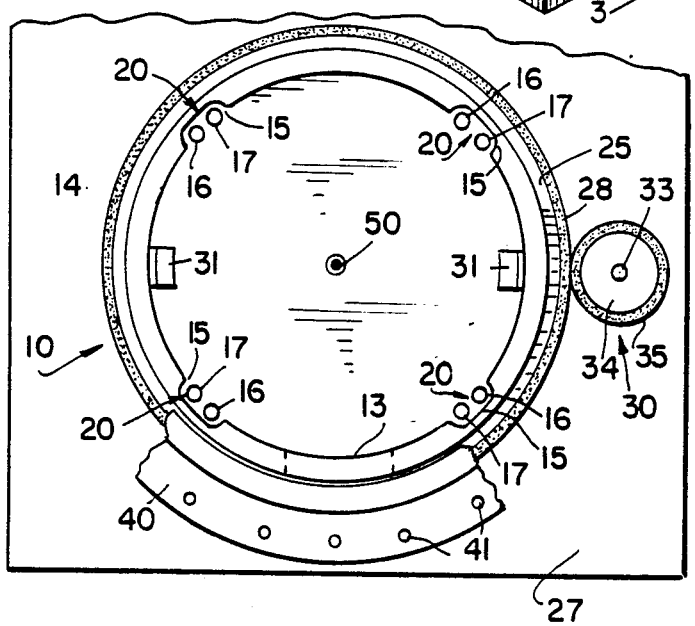
FIG. 2 is a top plan view of the tanning booth of FIG. 1.
Figure 3:
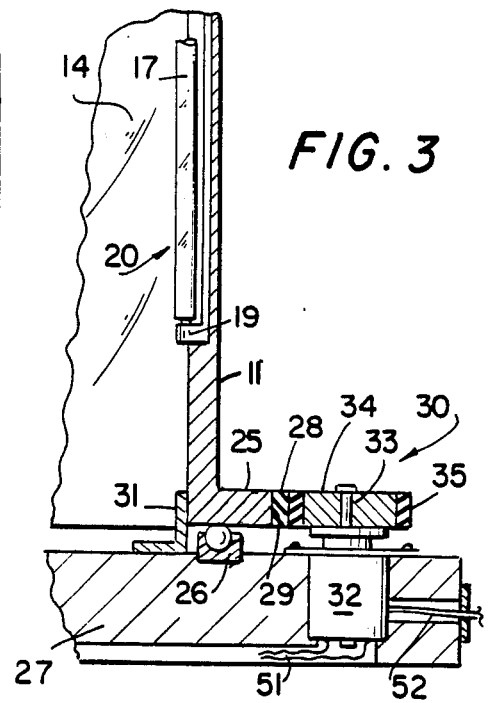
FIG. 3 is a partial sectional view taken along line 3—3 of FIG. 1.

The tanning booth of the present invention provides an even tanning by utilizing juxtaposed combinations of UVA and UVB lamps or an ultraviolet lamp specifically in the 300–340 nanometer (nm) range. The booth may be of cylindrical construction and rotatable to provide an even tan without requiring periodic movement by the user.

DESCRIPTION OF THE PERFERRED EMBODIMENTS

Referring to the FIGURES, there is shown the tanning booth of the present invention referred to as number 10. Booth 10 comprises a cylindrical chamber 11 formed of metal walk construction and having an anodized and polished aluminum sheet interior wall surface 14 for high 85% reflectivity. The cylindrical size is preferably 3'9" in diameter and 8 feet in height.

Chamber 11 is formed with access door 12, with the interior 13 of door 12 formed of similarly polished and anodized surface 14, so that when the door is closed the entire inner cylinder surface is reflective. Wall surface 14 is formed with a plurality, herein four, recessed portions 15. A set 20 of 6 foot long tubular lamps comprising one UVA lamp 16 and one UVB lamp 17, with respective ballasts 18 and 19, are vertically mounted in each of the recessed portions. The lamp sets 20 are electrically interconnected to timer control 21, which is selectively set by the operator before entering the booth.

Chamber 11 is mounted on and fixedly interconnected to flange member 25 which in turn rests on a plurality of sealed bearings 26, which, in turn, are supported by base 27. Retaining flanges 31 hold chamber wall 11 in position. Bearings 26 are circumferentially disposed so that cylindrical chamber 11 is free to rotate on its axis, for purposes hereinafter appearing.

Member 25 is formed with an annular rubber bumper 28 which is fixedly adhered or mounted to the peripheral edge 29 of member 25. A drive assembly 30, is mounted with bumper 28. Assembly 30 comprises a drive motor 32, with vertically upwardly disposed drive shaft 33 interconnected to horizontally disposed wheel 34 for constant speed rotation. Wheel 34 is formed with rubber bumper 35 on the periphery 36 of the wheel 34. Drive bumper 35 frictionally engages bumper 28, so that with rotation of wheel 34, member 25 and chamber 11 are rotated. Drive motor control switch 50 may be conveniently mounted for operation within the center of chamber so that the user can control the operation. A control connection 51 and power cord 52 are interconnected to drive motor 32 in the well known manner.

A step or shield 40 extends partially around chamber 11 and is fixedly mounted to the base 27 at 41, and disposed above rotatable flange member 25, so as to permit access to door 12 without stepping onto the rotatable member 25.

In the aforesaid manner, the operator sets control timer 21 to the appropriate setting for that user's needs. The user then steps on shield 40 and opens door 12 and enters chamber 11. UV lamp sets 20 are "on" as a result of the timer control operation. The user then positions himself or herself at or near the axis of the cylinder, and actuates rotation control switch 50 causing wall 12 with lamp sets 20 to rotate. Switch 50 may be interconnected to timer 21 to cause the timer to start and stop with rotation.

It has suprisingly been found that the use of combinations of UVA and UVB lamps provides an even and effective tanning, and the further combination of cylindrical chamber rotation provides a highly effective even tanning process.

The combination of UVB and UVA lamps has been found to create an optimum tanning effect, not present with use of only UVA and UVB lamps. In a preferred embodiment it has been found that more UVB lamps may be used than UVA lamps.

In the combined use of UVA and UVB lamps, the UVB lamps should be present in a greater number than the UVA lamps, and preferably at a UVB:UVA ratio of about 3:2. The lamps sets should be positioned side by side. The juxtaposed positions of the UVA and UVB lamps may preferably be reversed in diametrically opposed positions.

In another embodiment of the invention, UVA and UVB lamps are replaced with a single type of lamp. This latter said lamp provides ultraviolet rays in only, what has now been found to be, the critical specific range of 300–340 nm. Lamp design for a specific selected wave length range is well known in the art. This critical range has been found to provide an even, natural looking and long lasting tanning, while eliminating the drawbacks in using only UVA or UVB lamps.

Without wishing to be bound by any theory or mechanism it is believed that the tanning process comprises three process steps, namely, permeation, absorption and oxidation, which are dependent on three optimum points at different wave lengths, as follows:

(UVB) 1—optimum permeation dependency—300 nm.
(UVB) 2—optimum absorption dependency—below 320 nm.
(UVA) 3—optimum oxidation dependency—340 nm.

Thus, there is now provided a UV lamp in the 300–340 nm range. This lamp provides a relative increase in energizing effect with a relative decrease in wave length. By eliminating the excessive long waves, the tanning time is decreased while providing cooler temperatures in the booths. There is thus provided a safe environment by virtue of the decrease in effective tanning time with elimination of the more intense and penetrative radiations.

While the present invention preferably utilizes a cylindrical unit, where a rectilinear chamber is used a 3 foot square tubular construction is best employed.

Although the invention has been described with respect to a specific embodiment, it will be appreciated that modifications may be made by those skilled in the art without departing from the true spirit and scope of the invention.

What is claimed is:

1. A tanning booth comprising an enclosed chamber, and a plurality of lamps disposed in said chamber for tanning a person standing in said chamber, said lamps emitting a specific radiation range consisting essentially of 300–340 nm to provide a composite UVA and UVB tanning effect.

2. The tanning booth of claim 1, said lamps comprising UVA and UVB lamps.

3. The tanning booth of claim 2, wherein there are more UVB lamps than UVA lamps.

4. The tanning booth of claim 3, said chamber being an upright cylinder, and said lamps being elongated and vertically mounted on the interior of the cylinder.

5. The tanning booth of claim 4, a user base, and further comprising means to rotate said cylindrical chamber and said base, relative to each other, whereby the user being disposed about the axis of the cylinder is provided with an even tanning effect.

6. The tanning booth of claim 5, wherein there are more UVB lamps than UVA lamps.

7. The tanning booth of claim 2, said lamps are in a UVB:UVA ratio of about 3:2.

8. A tanning booth comprising a cylindrical chamber and a user base, ultraviolet lamps disposed in the cylindrical chamber and means to rotatably mount said chamber and the base relative to each other, and drive means to impart said relative rotation to said chamber and lamps or to said base, said lamps emitting radiation consisting essentially of 300–340 nm, whereby the user being disposed on the base about at the axis of the chamber is provided with an even composite UVA and UVB tanning effect.

9. The tanning booth of claim 8, said lamps comprise UVB lamps and UVA lamps.

10. The tanning booth of claim 8 said cylinder comprising reflective metal walls on the inside of the cylinder, and being formed with a plurality of longitudinally disposed recesses and wherein said lamps are mounted in said recesses.

* * * * *